United States Patent [19]

Man

[11] Patent Number: Plant 6,203

[45] Date of Patent: Jun. 14, 1988

[54] DISTINCT VARIETY OF BEGONIA PLANT NAMED ILONKA

[75] Inventor: Jan Man, Lisse, Netherlands

[73] Assignee: Oglevee Associates, Inc., Connellsville, Pa.

[21] Appl. No.: 885,487

[22] Filed: Jul. 14, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Webb, Burden, Robinson & Webb

[57] ABSTRACT

A new Begonia variety is characterized by its superior growth and flowering. The overall appearance is very pleasing with a strong contrast between the light peach color of the bloom and the dark green color of the foliage. The new cultivar has a high tolerance to botrytis and powdery mildew.

1 Drawing Sheet

BACKGROUND OF THE NEW PLANT

The present invention comprises a new and distinct cultivar of *Begonia*×*hiemalis* known by the varietal name of Ilonka. The new cultivar is a selection of a cross between the seed parent Lara and the pollen parent Ilona. The new cultivar has the same foliage and form as Ilona; however, Ilonka has large double flowers whereas Ilona has small single flowers.

The new cultivar was discovered in September of 1982 at Limaplant b.v. in Lisse, Holland; was first asexually reproduced by cuttings at Limaplant b.v. in Lisse, Holland; and has been repeatedly asexually reproduced by cuttings for Oglevee Associates, Inc. in Connellsville, Pa. It has been found to retain its distinctive characteristics through successive propagations.

The new cultivar is generally characterized by its superior growth and flowering. The overall appearance is very pleasing with a strong contrast between the light peach color of the bloom and the dark green color of the foliage. The new cultivar has a high tolerance to botrytis and powdery mildew.

The new cultivar, when grown in a greenhouse in Connellsville, Pa., has a response time of nine to ten weeks from a well-rooted cutting to a flowering finished plant in a six inch pot (no pinch).

DESCRIPTION OF THE DRAWING

The accompanying drawing illustrates a new cultivar, the color being as nearly true as possible with color illustrations of this type.

DESCRIPTION OF THE NEW PLANT

The following detailed description sets forth the characteristics of the new cultivar. The data which define these characteristics were collected from asexual reproductions carried out for Oglevee Associates, Inc. in Connellsville, Pa. The plant history was taken on ten week plants blossomed under natural light in a greenhouse and grown under temperature conditions of 62° F. at night and 68° F. during the day. The plants were potted in a peat-lite mix and fertilized with a 100 ppm mixture of 15N-0P-15K. Color readings were taken indoors under 200 footcandles of cool white fluorescent tubes. Color references are to the R.H.S. Colour Chart of The Royal Horticultural Society of London, unless noted differently.

Botanical classification: *Begonia*×*hiemalis*.

Flower:

- *Fully expanded.*—6 cm in diameter.
- *Buds.*—2–3 cm wide.
- *Borne.*—Compound dichasium (cyme).
- *Stems.*—Stems are strong and upright, main stem 8 mm in diameter; color 144C on young growth; older growth has red overtones (the older the stem, the more red is present).
- *Form.*—Semi-double to fully double. Each flower generally has 2 sepals, 7 petals, 7 petaloids (each group may vary±1 structure).
- *Permanence.*—Long lasting bloom, generally each individual flower will remain fresh for 2–3 weeks.

Color:

- *Tonality from a distance.*—Peach.
- *Front of petals.*—Color gradient pink→light orange→yellow-green; outer edge: red group 38B; middle: orange-red group 32C; inner: yellow-orange group 23C.
- *Reverse of petals.*—Red group 38B.
- *Base of petals.*—Yellow-green group 151B.
- *Throat.*—None.
- *Discoloration.*—None.
- *Other comments.*—Difficult to be exact because of color gradients and age variation among flowers (color changes as flower ages).

Petals:

- *Appearance.*—Oval with color gradient.
- *Arrangement.*—Fully double.
- *Persistence.*—Very good, flowers last long time and plant will continue to produce new buds.
- *Fragrance.*—None.

Reproductive organs: All reproductive organs have modified into petaloids. Anthers, filament, pollen and style could not be observed.

Plant:

- *Form.*—Short, compact, internodes 2–3 cm apart, good basal branching, strong stems give good self-support.
- *Growth.*—Very vigorous, growth can be modified by changing environmental conditions (higher temperature will give faster and lusher growth).
- *Height from soil line.*—12–14 cm in 10 weeks (no pinch, no cycocel).

*Spread.*—22–24 cm in 10 weeks (no pinch, no cycocel).

Foliage:

*Size.*—Depends upon position and growth. Average length of 12 cm and average width of 8 cm.

*Quantity.*—Very abundant.

*Shape.*—Acute tip with irregularly lobed attachment; edge is doubly serrate.

*Top side.*—Green group 139A.

*Underside.*—Green group 137C.

*Ribs and veins.*—Smooth on top, raised on bottom. Palmate in arrangement. Lower side veins only area where visible tricomes (hairs) appear.

*Rib and vein color.*—Top: yellow-green group 145G; bottom: yellow-green group 146D.

*Margin.*—None.

*Stipules.*—None.

*Texture.*—Top: leathery and glabrous; bottom: matt finish with raised veins.

I claim:

1. A new and distinct variety of Begonia characterized by its superior growth and flowering, very pleasing overall appearance with a strong contrast between the light peach color of the bloom and the dark green color of the foliage, and high tolerance to botrytis and powdery mildew as herein shown and described and parts therefor.

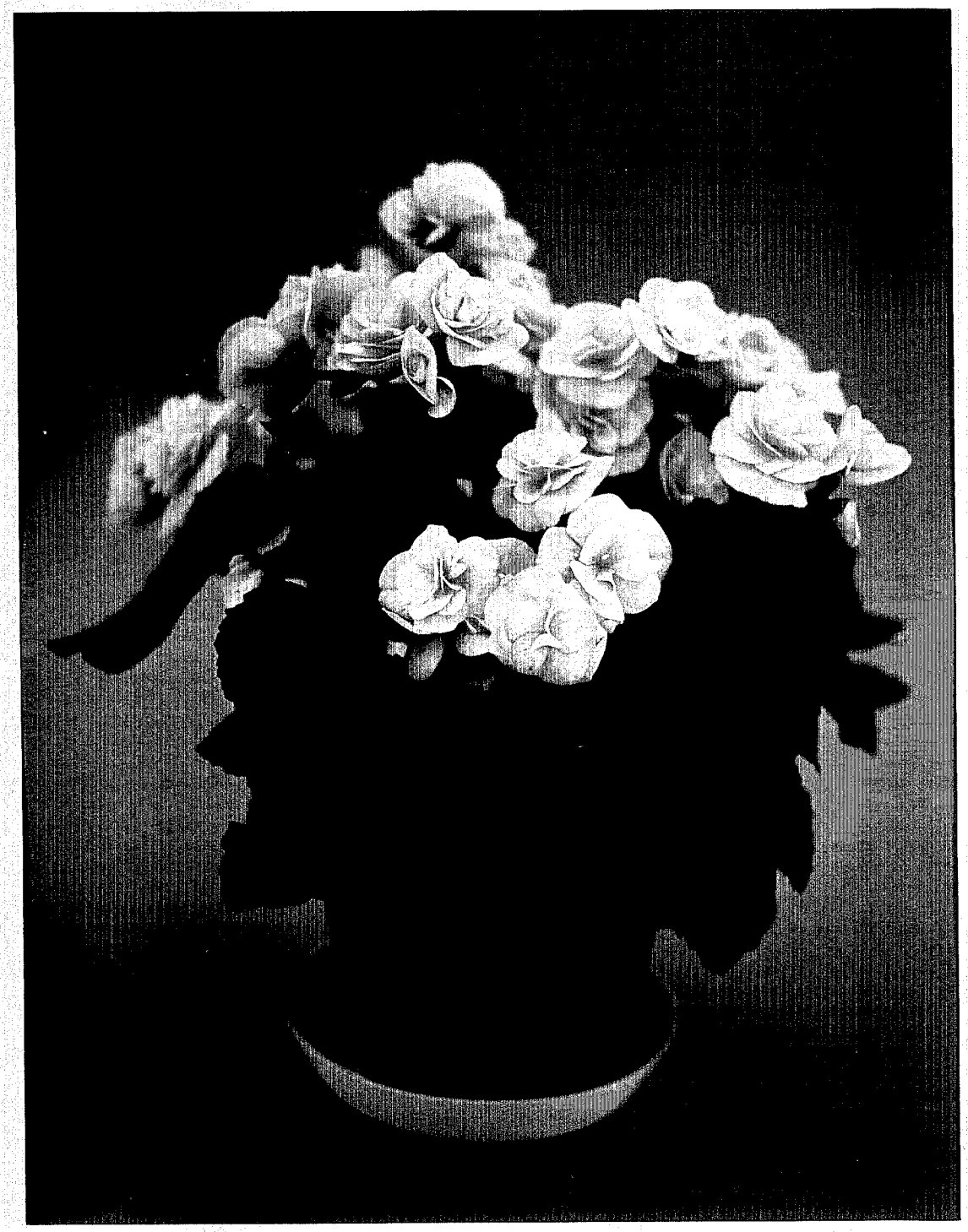

* * * * *